(12) United States Patent
McSpadden

(10) Patent No.: US 6,293,794 B1
(45) Date of Patent: Sep. 25, 2001

(54) ENDODONTIC INSTRUMENT HAVING REGRESSIVE CONICITY

(75) Inventor: John T. McSpadden, Lookout Mountain, GA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 09/252,601

(22) Filed: Feb. 16, 1999

(51) Int. Cl.$^7$ ............................................. A61C 5/02
(52) U.S. Cl. .................................................. 433/102
(58) Field of Search ........................................ 433/102

(56) References Cited

U.S. PATENT DOCUMENTS

| | | | |
|---|---|---|---|
| 443,297 | 12/1890 | Sellers | 408/213 |
| 453,254 | 6/1891 | Bryant | 433/65 |
| 1,211,537 | 1/1917 | Burton | 175/392 |
| 2,035,298 | 3/1936 | Caldwell | 408/212 |
| 2,084,737 | 6/1937 | Reamer | 77/72 |
| 2,328,629 | 9/1943 | Eich et al. | 145/117 |
| 2,769,355 | 11/1956 | Crisp | 77/70 |
| 2,966,081 | 12/1960 | Kallio | 77/70 |
| 3,387,511 | 6/1968 | Ackart, Sr. et al. | 77/70 |
| 3,443,459 | 5/1969 | Mackey et al. | 77/70 |
| 3,947,143 | 3/1976 | Gulla | 408/230 |
| 3,971,135 | 7/1976 | Leu | 433/65 |
| 3,991,454 | 11/1976 | Wale | 29/105 R |
| 4,209,275 | 6/1980 | Kim | 408/211 |
| 4,330,229 | 5/1982 | Croydon | 408/212 |
| 4,332,561 | 6/1982 | McSpadden | 433/102 |
| 4,457,710 | 7/1984 | McSpadden | 433/81 |
| 4,538,989 | 9/1985 | Apairo, Jr. | 433/102 |
| 4,602,900 | 7/1986 | Arpaio, Jr. | 408/230 |
| 4,894,011 | 1/1990 | Johnson | 433/81 |
| 4,904,185 | 2/1990 | McSpedden | 433/164 |
| 5,035,617 | 7/1991 | McSpadden | 433/102 |
| 5,106,298 | 4/1992 | Heath | 433/102 |
| 5,230,593 | 7/1993 | Imanaga et al. | 408/230 |
| 5,236,357 | 8/1993 | Randin | 433/102 |
| 5,257,934 | * 11/1993 | Cossellu | 433/102 |
| 5,658,145 | * 8/1997 | Maillefer et al. | 433/102 |
| 5,752,825 | * 5/1998 | Buchanan | 433/102 |
| 5,836,764 | * 11/1998 | Buchanan | 433/102 |

\* cited by examiner

*Primary Examiner*—John J. Wilson
(74) *Attorney, Agent, or Firm*—Wood, Herron & Evans L.L.P.

(57) ABSTRACT

A method and apparatus for extirpating tissue from a radicular dental canal comprises a set of instruments having graduated lengths and diameters. In one embodiment of the invention, one instrument is of such length to extirpate the apical foramen. This full depth instrument has a first cutting length that conforms to a first taper angle between a conical apex and a first base diameter. The first cutting length is less than the length of the root canal. Above the first cutting length, the instrument may be cylindrical. The full depth instrument is followed by a second instrument having a length that is less than that of the full length instrument by the length of the first cutting length. The second instrument cutting length is also less than the length of the root canal and extends between a minor diameter at the tip of the instrument and minor diameter at the longitudinal end of the cutting length. The second instrument minor diameter is substantially the same as the major diameter of the full depth instrument.

17 Claims, 5 Drawing Sheets

ENDODONTIC INSTRUMENT HAVING REGRESSIVE CONICITY

BACKGROUND OF THE INVENTION

The present invention relates generally to the field of dental instruments. More particularly, the invention relates to those instruments used in the practice of endodontia to remove dead or damaged tissue from a tooth root canal preparatory to filling the root canal.

Extraction of a tooth may often be avoided by removing decayed, damaged, or dead tissue from the nerve canal within a tooth root. Typically, to remove decayed, injured or dead tissue from the root canal of a tooth, an endodontist will first drill into the tooth to locate the root canal and thereafter use instruments of small diameter, such as reams and files, to remove the decayed, injured or dead tissue from the nerve canal. The objective of tissue removal with the instrument is to produce a funnel-shaped canal, with the smaller end at the apical foramen, so as to provide the canal with a desirable form for filling. Such root canals are not necessarily straight. The instrument must be able to follow a curved path as it is moved through the canal for purposes of removing the tissue. Therefore, the instrument must be flexible yet possess sufficient strength so that it is not easily broken when stroked and rotated through a root canal.

Commonly, both files and reamers have flutes which spiral along a portion of the instrument length. Whether the instrument is considered to be a file or a reamer is determined by the pitch of the flutes. A greater pitch enables the instrument to cut better in a rotary mode. Hence, a large pitch instrument is characterized as a reamer. A lesser pitch to the endodontic instrument flutes enables the instrument to cut better in the reciprocating mode of motion. A low pitch instrument is therefore characterized as a file. During a cleaning and shaping operation performed with an endodontic file or reamer, the instrument is normally rotated and reciprocated into and out of the root canal along the longitudinal axis of the instrument. Therefore, even during rotational movement of a reamer through a canal the instrument is commonly reciprocated to a degree to effect the desired cut. Similarly, a file is commonly rotated slightly as it is reciprocated longitudinally.

In order for the instrument to extirpate root canal tissue as it is rotated and moved longitudinally, relatively high torsion forces must be typically applied to the instrument. These high torsional loads on the instrument may lead to torsional failure of the instrument. In addition, the curved path of common root canals requires that the instrument concurrently be subject to bending and torsional loads as it is moved along the canal. This combination of bending and torsional loads as the instrument is moved along the canal increase the likelihood of torsional failure.

Traditional ISO Standard files for endodontia have a taper angle of about two percent. This taper is usually continuous over the full working length of the file. Size of the file is based upon the file tip diameter. Using ISO Standard files, a "crown down" technique of radicular extirpation begins by first penetrating the root canal with a large diameter instrument followed sequentially by one or more files of diminishing diameter until the apical foramen is reached. As the root canal bore is extended toward the root apex, the active cutting proportion of the file working length increases while, at the same time, the file size and tip diameter is diminishing. This increase in the active cutting portion of the file necessarily results in an increase in the torque stress imposed on the file and on the probability of file failure.

Another approach for radicular extirpation is based upon use of several files having the same maximum diameter but with a graduated series of decreasing taper angles from the file tip that terminate at the maximum diameter. The canal is started with the file of greatest taper angle. The first file is advanced to a depth corresponding to the desired entrance diameter. The second file, having a smaller angle of tapered convergence from the tip to the maximum diameter, has a greater axial length from the maximum diameter base to the file tip. Hence, the second file will advance the canal depth from the same entrance diameter. This procedural sequence will continue down to the apical foramen. Similar to the "crown down" procedure, the decreasing taper angle method of extirpation imposes greater torque on the most fragile files.

It is therefore, an object of the present invention to provide an improved method of radicular extirpation that operatively limits the magnitude of torque imposed on a root canal file.

Another object of the invention is a set of root canal instruments for carrying out the improved method of the invention.

A further object of the invention is a root canal instrument set that operatively limits the magnitude of torque that is likely to be imposed on each instrument in the set.

SUMMARY OF THE INVENTION

These and other objects of the invention as will be apparent from the following description of the preferred embodiments are carried out by an endodontic procedure in which the magnitude of torque imposed on each instrument in a graduated set is inherently limited by the instrument design.

For reference, instruments according to the invention are rotary cutting devices having tissue cutting edges formed about the axis of substantially conical or cylindrical shaft to surfaces. That axial length portion of an instrument provided with cutting edges is normally characterized as the "working surface" of the instrument. A substantially smooth surface, axial extension of the instrument shaft from the working surface is often characterized as the "shank." The functional purpose of a shank is for direct engagement with an instrument motor drive chuck. At the axial end of the instrument opposite from the shank is the leading tip of the instrument. The length of working surface behind the tip is characterized as "the cutting surface." Although the instrument working surface includes cutting edges throughout, that portion of the working surface specifically intended for insitu tissue engagement represents the cutting surface. The cutting surface of an instrument may be all or less than the length of the working surface.

Each instrument in a set according to the invention is formed with a predetermined magnitude of cutting surface as distinguished from the working surface. With respect to each instrument in the set, the cutting surface is developed about the instrument axis at a predetermined taper angle. The axial length of the cutting surface is preferably determined between a minor (smaller) diameter and a major (greater) diameter respective to the instrument cross-section. The working surface of the instrument from the major diameter toward the instrument shank may continue with a second taper angle. Additionally, the minor diameter of each instrument in the sequential set substantially corresponds to the major diameter of the preceding instrument in the set.

The taper angle respective to the cutting surface of all instruments in the set may be substantially the same or graduated. Additionally, the length or area of a cutting surface for each instrument in a set is about the same as for other instruments in the same set.

In practice, the root canal may be initially opened by the first instrument with a pilot boring down to the apical foramen. This first instrument may have a shank and working surface diameter that is substantially the same as the cutting surface major diameter. The minor diameter is substantially the apex of the first taper angle. Accordingly, drive torque to the canal starting instrument is essentially limited to that exerted by the limited area of the first cutting surface. Moreover, this limited torque is transmitted along a substantially constant shaft diameter of relatively substantial size thereby minimizing the probability of shaft failure.

The second instrument in the set has a minor diameter at its tip that is substantially the same as the major diameter for the first instrument. The second instrument working portion from the second major diameter preferably is a straight shaft cylinder.

The foregoing pattern of the minor diameter of a subsequent instrument cutting surface as corresponding to the major diameter of the prior instrument cutting surface is repeated out to the root canal opening. Simultaneously, the axial length of each instrument from a common indicia reference is preferably reduced by about the same amount as the length of the preceding instrument cutting surface.

When gaging rings or other such positional reference indicia are provided around the instrument shanks at a uniform position for all instruments in the set, the physician may judge when he has reached the appropriate bottom depth for each instrument. Resultantly, the canal is given a uniform taper angle from the apical foramen to the canal entrance.

BRIEF DESCRIPTION OF THE DRAWINGS

Relative to the drawings wherein a reference character designates the same or similar elements throughout the several figures of the drawings.

DESCRIPTION OF THE PREFERRED EMBODIMENTS

Figure 1:
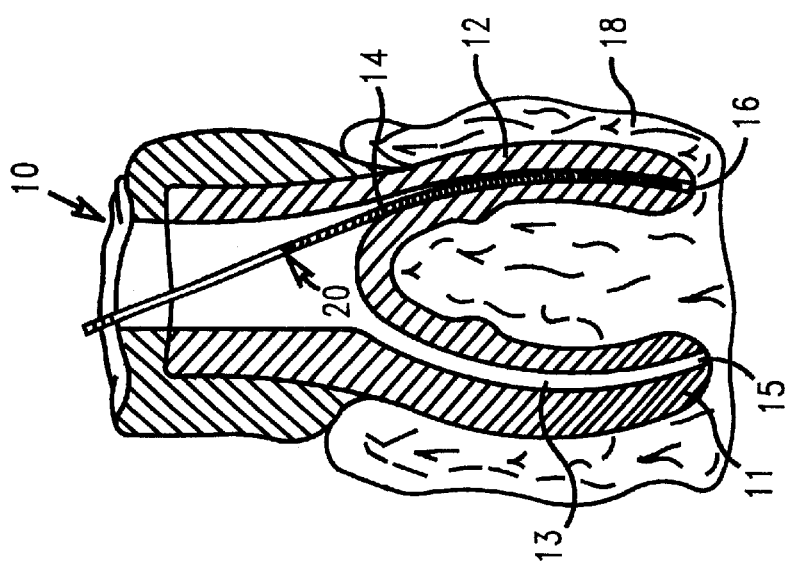
FIG. 1 is a cross-sectional view of a tooth having two roots and an endodontic instrument positioned along the nerve canal in one of the root canals

The specific utility environment of the invention is represented by the FIG. 1 illustration of a tooth 10 cross-section held by roots 11 and 12 in living bone tissue 18. Characteristically, each root has a nerve canal 13 and 14, respectively. At the distal end of each root, the nerve canals 13 and 14 terminate at respective apical foramen 15 and 16. The radicular extirpation medical procedure commonly known as a root canal requires that the root canal nerve be cleaned of soft tissue, sterilized and filled with a firm antiseptic filling material such as gutta percha. The tissue removal step of the procedure is carried out by the use of an endodontic instrument 20 that may also be described as a file or reamer. This instrument 20 is an elongated shaft that traditionally has a substantially uniform cross-section about a longitudinal axis of rotation. Typically, the shaft 20 is about 30 mm long or less and about 0.5 mm to about 1.6 mm diameter.

Manipulation of the instrument 20 pursuant to tissue extirpation normally includes a combination of movements such as a rotation and oscillation of the instrument about the shaft axis and translation along the axis. Although the manipulations are performed manually by the orthodontist in any case, in some circumstances the rotational torque is applied to the instrument by means of a handgrip of some form. In other cases, the orthodontist may connect the instrument shaft to a motor. Neither a handgrip nor a motor is illustrated but those of knowledge in the art are familiar with both rotational drive devices.

Figure 2:
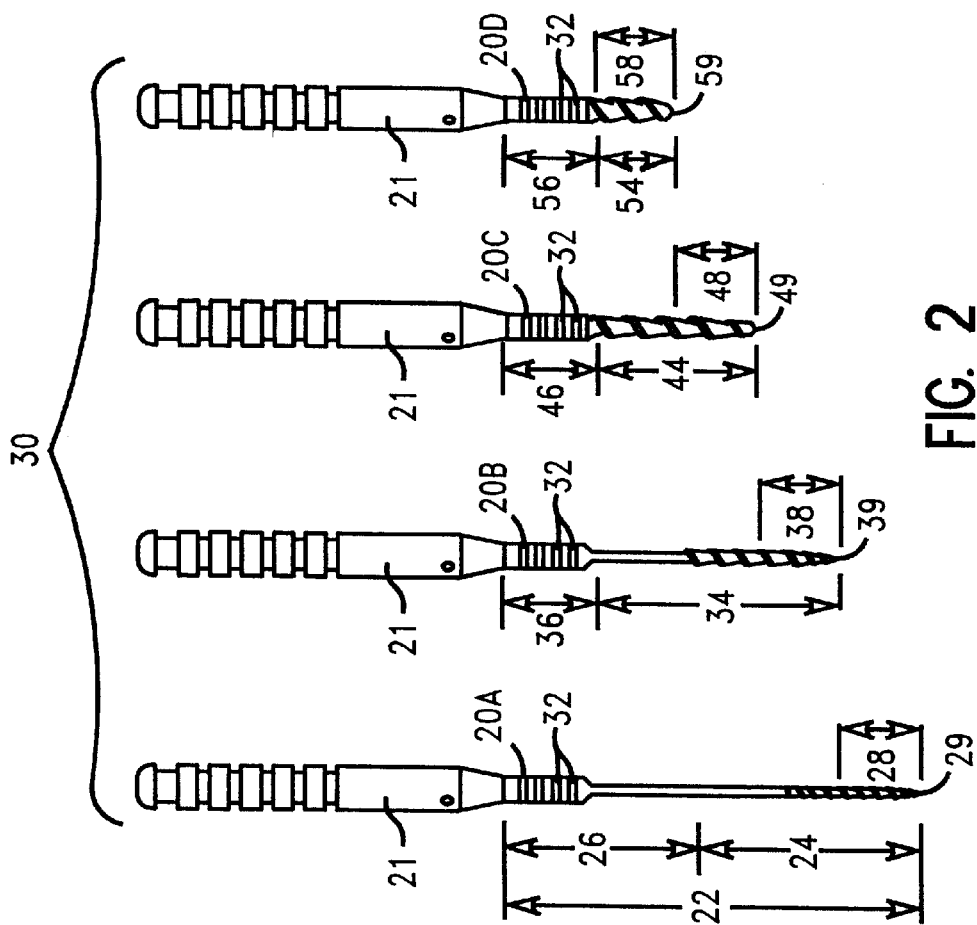
FIG. 2 is a side view of a first instrument set.

Referring now to FIG. 2, the invention is represented by a set of endodontic instruments 30 comprising, for example, four instruments 20A, 20B, 20C and 20D in a graduated series. Each of the instruments 20A–20D is secured to a chuck coupling 21 by which rotational torque may be transmitted to the respective instrument shaft 22.

The shaft 22 of each instrument 20 among the set 30 comprises a working surface, a cutting surface and a shank portion. With respect to the first instrument 20A, the working surface 24 of the shaft 22 is helically fluted to facilitate removal of the extirpated tissue. A shank 26 extends from the working surface 24 for connective interface with the chuck coupling 21. Indicia such as rings 32 are often cut into the shank 26 surface as reference marks by which the orthodontist may judge the depth of shaft tip 29 penetration along the root canal 14 relative to a fixed point on the tooth structure.

Figures 3, 4, 5:
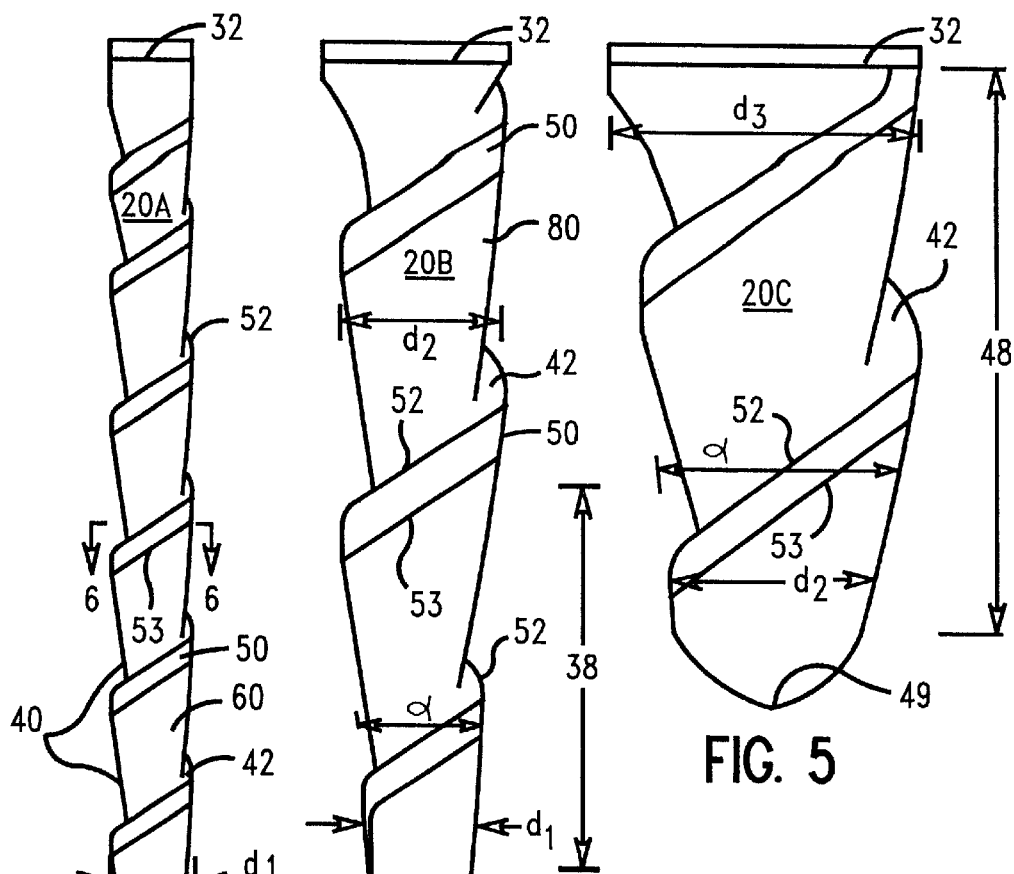
FIG. 3 is an enlarged side view of a first instrument in a set.
FIG. 4 is an enlarged side view of a second instrument in a set.
FIG. 5 is an enlarged side view of a third instrument in a set.
Figure 6:
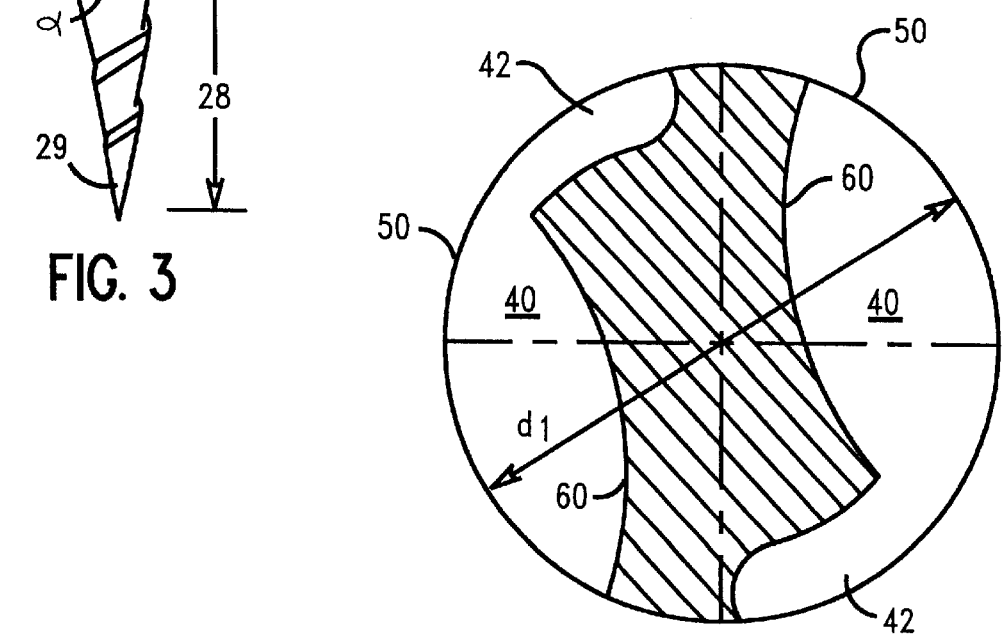
FIG. 6 is a cross-sectional view into the cutting plane 6—6 of FIG. 3.
Figure 7:
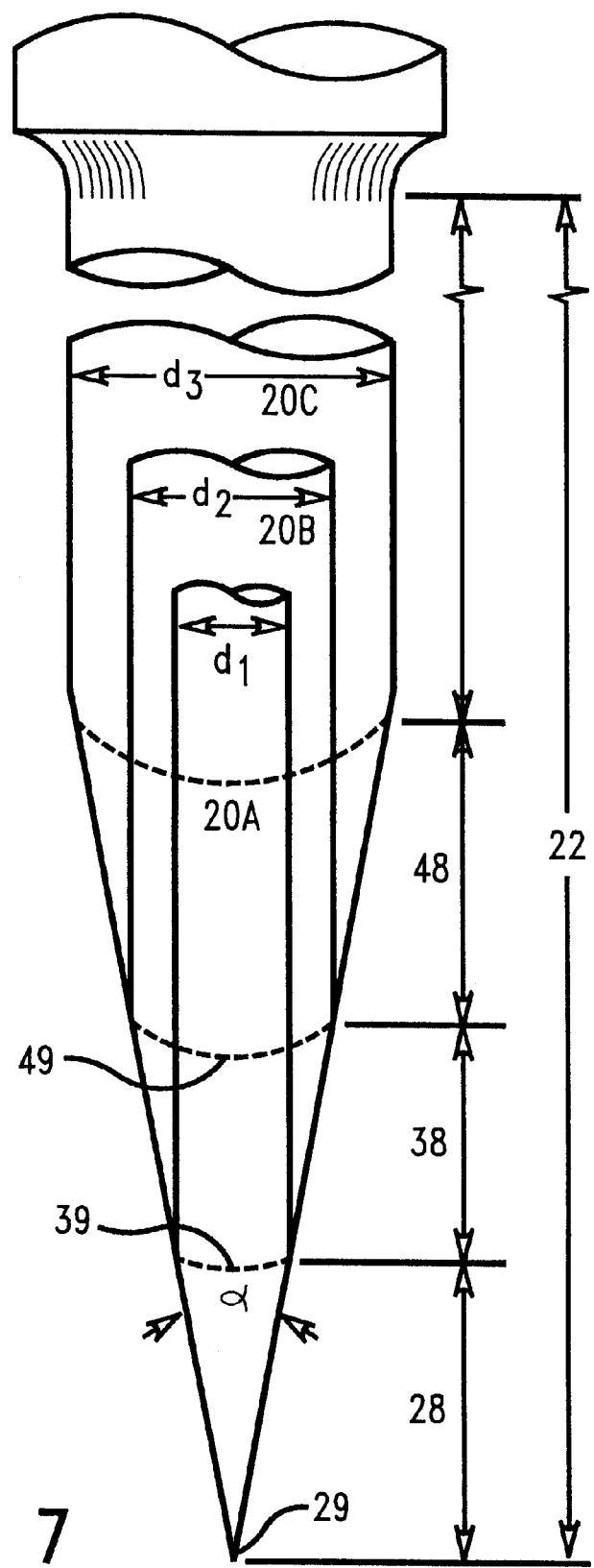
FIG. 7 is a superimposed profile of a first invention embodiment.
Figure 8:
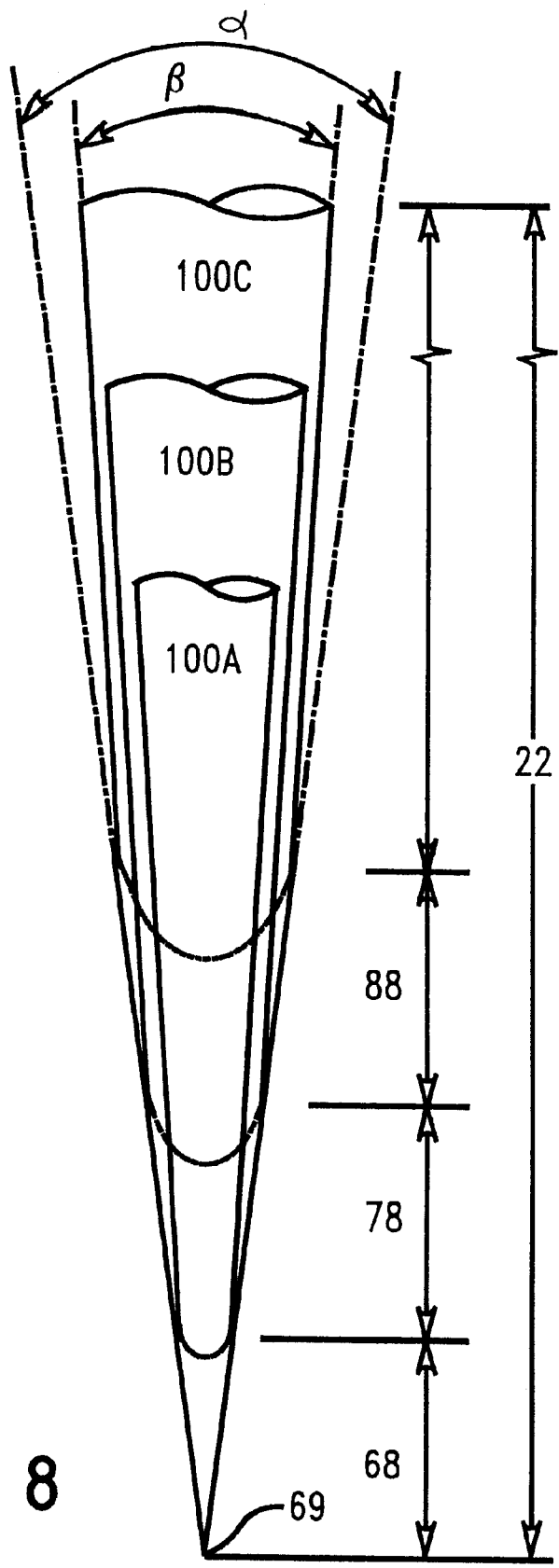
FIG. 8 is a superimposed profile of a second invention embodiment.

As most clearly shown by FIGS. 3 and 7, the cutting surface 28 of the first or pilot instrument 20A is a portion of the working surface 24, but is distinctive by a tapered surface profile that conforms to a conical angle $\alpha$. The cutting surface angle $\alpha$ is greater than the included angle of the working surface 24 remainder. In the embodiment of the invention shown by FIGS. 3 and 5, the remaining working surface 24 is cylindrical having a zero taper angle. An alterative embodiment of the invention as shown by FIG. 8, however, continues the working surface at a reduced conical angle $\beta$. With resumed reference to the FIGS. 3 and 7, the conical angle $\alpha$ for the pilot instrument 20A defines a cutting surface 28 that begins with an approximate apex 29 at the shaft tip and continues to a major diameter $d_1$. The diameter $d_1$ corresponds to the cylinder diameter for the remaining working surface 24 and is the conical truncation base for the cutting surface 28 cone.

Characteristic of the working surfaces are one or more helical fluctuates 40 as shown by FIGS. 3 through 6. Whether the helical twist is right-hand or left-hand is a matter of choice determined by a preferred rotational direction for debris removal. The flute profiles are defined by helical walls 60 that slope from a peripheral land 50 toward the shaft tip and axis. The radially internal base of the wall 60 junctures with a helically wound shoulder 42. Relative to the cutting edge 52 of the peripheral land 50, the shoulder 42 is undercut with a radial slope from the perimeter edge 52 toward the shaft tip.

The peripheral land 50 has a cylindrical surface flat between the cutting edge 52 and the intersection edge 53 of the flute wall 60. This surface flat 50 functions to minimize excessive root canal enlargement on the inside arc surfaces where the instrument shaft must bend to follow the curvature of a root canal. The width of this flat 50 may be progressively diminished as the surface winds toward the instrument tip and around the cutting surface 28.

The width of the helical shoulder 42 may also be given a graduated width between the perimeter cutting edge 52 and the juncture with the flute wall 60. For example, the shoulder 42 width may be increased as a percentage of the perimeter radius as the flute 40 progresses from the major diameter d, toward the shaft tip 29.

Returning to the first embodiment set 30 of FIG. 2, the pilot instrument 20A is turned into the root canal 14 completely to the apical foramen 16 as shown by FIG. 1. Although the pilot instrument cutting surface 28 is sufficient to extirpate the distal end of the root canal 16, the major diameter d, along the shaft working surface 24 of the pilot instrument is insufficient to radially clean the canal 16 above more than about 2 cm of canal length. Consequently, the pilot instrument 20A must be followed by sequentially larger instruments 20B, 20C and possibly 20D (FIG. 1). However, as the pilot instrument 20A is rotated and oscillated to cut the initial channel through the tissue within the canal 16, the cutting surface face is limited to the first tapered surface 28. Consequently, the torque imposed upon the instrument 20A shaft is limited to that transmitted through the cutting surface 28. As the instrument 20A progresses into the canal 16, any torque increase after full engagement by the cutting surface is substantially nominal.

When the pilot instrument tip 29 has extirpated the root canal end 16, the pilot instrument 20A is withdrawn to be succeeded by the second instrument 20B. The second instrument 20B in the set 30 differs from the pilot instrument 20A by both the length and diameter of the shaft. The shaft of instrument 20B has a length to the shaft tip 39, as measured from a particular reference indicia that is less than the corresponding length of instrument 20A by the cutting surface length 28. Preferably, the shaft tip 39 is non-cutting to reduce the instrument capacity and probability of undesirably enlarging a canal or starting a spurious channel.

With respect to FIGS. 4 and 7, it is to be noted that the minor diameter $d_1$ near the tip 39 of the instrument 20B cutting surface 38 is substantially the same as the major diameter $d_1$ for the pilot instrument 20A cutting surface 28. This relationship is illustrated dramatically by the superimposed schematic of FIG. 7 which shows the cutting surface 38 as having substantially the same conical angle α as the pilot cutting surface 28. If the major diameter $d_1$ of the pilot cutting surface 28 is substantially the same as the minor diameter $d_1$ of the second cutting surface 38, each surface, therefore, will be a sector of the same conical continuity.

As a further element of the invention, the length of cutting surface 38 may be substantially related to the length of cutting surface 28 by a substantially constant drive torque. This objective may be pursued along any of several design principles such as a constant conical surface area for each cutting surface sector. Alternatively, the axial length of each sector may be related to the length of cutting edge 52 whereby the length of cutting edge 52 is substantially the same for each section.

FIG. 5 illustrates the third element 20C of the instrument set 30 as having a cutting surface 48 extending as a conical frustum with an included conical angle α between a minor diameter $d_2$ and a major diameter $d_3$. The minor diameter $d_2$ of cutting surface 48 corresponds to the major diameter $d_2$ of cutting surface 38. However along the cutting surfaces 38 and 48, as measured from a particular reference indicia 32 on the shaft shank, the working length of a corresponding shaft 20B or 20C is preferably less than the working length of the preceding shaft by the length of the preceding cutting surface. The instrument tip 49 is preferably non-cutting.

FIG. 8 illustrates a regressive conicity embodiment of the present invention wherein the instrument shaft above the cutting surface follows a tapered enlargement along an angle β that is less than the cutting surface angle α. This FIG. 8 embodiment of the invention maximizes the shaft strength above the instrument cutting surface without increasing the cutting drive torque. Following the pilot cut of instrument 100A from the apex 69 along the cutting surface 68 at angle α, the succeeding instrument 100B expands the canal with a cutting surface section 78. Instrument 100C succeeds instrument 100B with a cut along cutting surface section 88. The major diameter to each of these cutting surface sections delineates the length of the cutting surface and the start of the angle β shaft taper.

Figure 9:
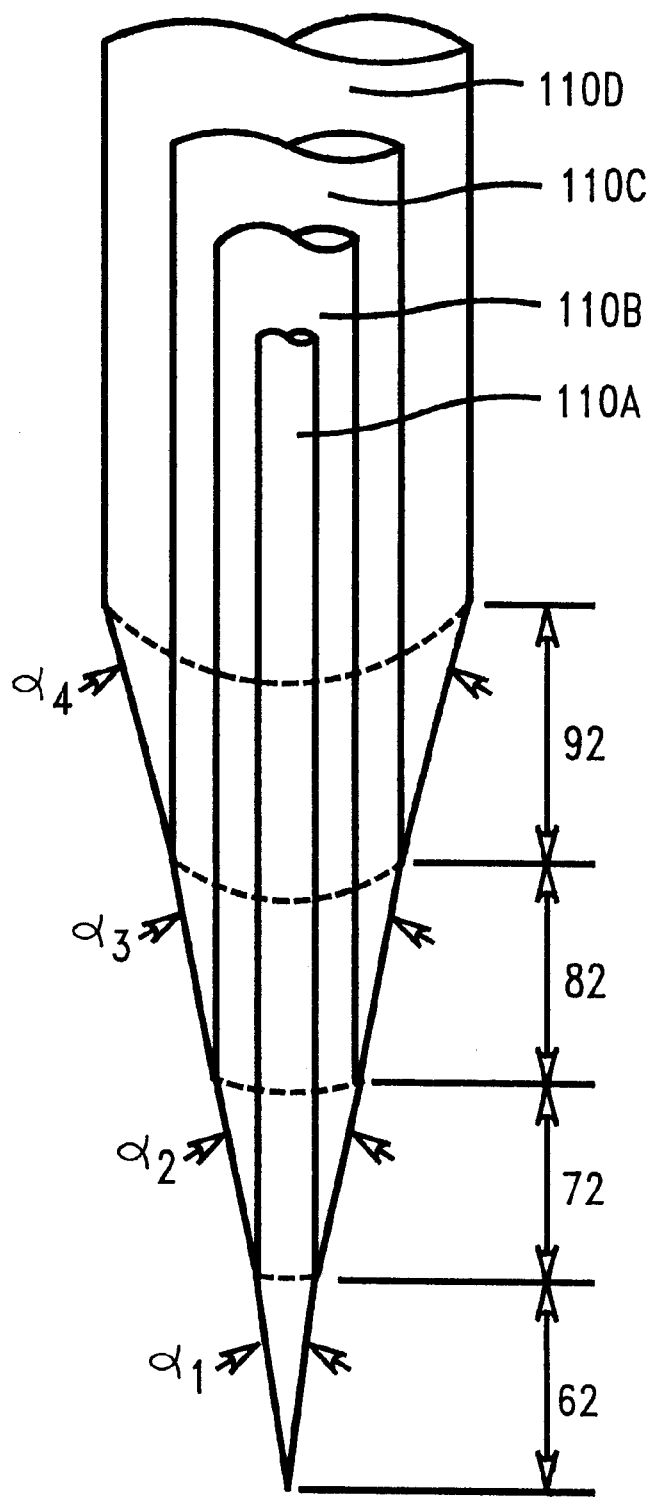
FIG. 9 is a superimposed profile of a third embodiment of the invention.

The invention embodiment of FIG. 9 represents a set of four instruments, 110A, 110B, 100C and 100D having cutting surface angles respective to each of the cutting surfaces 62, 72, 82 and 92. For example, the first cutting surface 62 may be given a taper angle $\alpha_1$ of about 1%. The second cutting surface 72 corresponds to instrument 110B may have a taper angle $\alpha_2$ of about 3%. The third cutting surface 82 of instrument 110C may have a taper angle $\alpha_3$ of about 4%. The fourth cutting surface 92 of instrument 110D may have a taper angle $\alpha_4$ of about 5%. Hence, the cutting surface taper angles respective to the several instruments in a set may differ. However, not withstanding differences in respective taper angles, the minor diameter of a successive instrument, 72 for example, is substantially the same and substantially coincides with the major diameter of the preceding instrument 62.

In another, none-illustrated example, a set may comprise three instruments wherein the first cutting surface is given a 4% taper angle from a non-tapered shank. The second instrument may have a cutting surface of only a 2% taper angle from a non-tapered shank. The third instrument may have a cutting surface of about 6% taper angle from a non-tapered shank.

Preferred embodiments of the invention have described endodontic procedures, that begin with an initial penetration of the root canal down to the apical foramen followed by successive extirpation increments up to the tooth crown. It will be understood by those of ordinary skill in the art that this sequence may be reversed. In such case, the crown would be opened first to substantially full volume. Following extirpation of the crown increment, a second root canal segment is extirpated for coincidence of the second segment major diameter with the first segment minor diameter. The third root canal segment is extirpated for coincidence of the third segment major diameter with the second segment minor diameter.

The foregoing description of preferred embodiments for my invention has been presented for purposes of illustration and description. These embodiments are not intended to be exhausted or to limit the invention to the precise forms disclosed. Obvious modifications or variations are possible in light of the above teachings. The embodiments were chosen and described to provide the best illustrations of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with breath to which they are fairly, legally and equitably entitled.

I claim:

1. A sequential plurality of endodontic instruments comprising a set for extirpating radicular dental canals, each instrument in said set having a working length that includes a shank portion and a tapered end portion, said tapered end portion having a diminishing diameter along a cutting length between a first diameter and second diameter, said first diameter being proximate of a region of integral juncture of said tapered end portion with said shank portion and said second diameter being proximate of a tapered end portion terminus, the second diameter for a first instrument in the sequential plurality of said set substantially being an apex terminus and subsequent instruments in the sequence having a second diameter substantially corresponding to the first diameter of a sequentially adjacent instrument, wherein the working length of each subsequent instrument in said set is less than the working length of a sequentially adjacent instrument by a distance that substantially corresponds to the cutting length of the tapered end portion of said sequentially adjacent instrument.

2. A set of endodontic instruments as described in claim 1 wherein the tapered end portion of each instrument in said set substantially conforms to a respective conical angle.

3. A set of endodontic instruments as described by claim 2 wherein the tapered end portion of all instruments in said set substantially conform to the same conical angle.

4. A set of endodontic instruments as described by claim 2 wherein the tapered end portion of each instrument in said set substantially conforms to a different conical angle.

5. A set of endodontic instruments as described by claim 1 wherein a first conical angle respective to the tapered end portion of an instrument is substantially the same for all instruments in said set.

6. A set of endodontic instruments as described by claim 5 wherein outer surface elements about a perimeter of said shank portion are substantially parallel.

7. A set of endodontic instruments as described by claim 5 wherein outer surface elements about a perimeter of said shank portion substantially circumscribe the frustum of a cone having a second conical angle that is less than said first conical angle.

8. A set of endodontic instruments as described by claim 1 wherein a terminal end portion respective to subsequent instruments in the sequence comprises non-cutting surfaces.

9. A set of endodontic instruments as described by claim 1 wherein the second diameter for subsequent instruments in said sequence circumscribes a non-cutting tip.

10. A method of extirpating radicular dental canals comprising the steps of:

extirpating tissue from a root canal length along a first boring that substantially terminates proximate of a distal tip of the canal with a first instrument having a tapered end portion with a cutting length forming a substantially conical first extirpation volume, said first extirpation volume expanding from a substantial apex with a first conical angle along a first conical length less than said root canal length to a first conical base having a first canal diameter; and, extirpating tissue from said root canal along said canal length in at least one different conical length increment with a second instrument having a second working length, said different conical length increment being less than said canal length and delineating a conical frustum having said first conical angle and said second working length being less than said first working length by a distance that substantially corresponds to the cutting length of the tapered end portion of said first instrument.

11. A method as described by claim 10 wherein the conical frustum respective to each of said different length increments has a major diameter at one end of said length increment and a minor diameter less than said major diameter at an opposite end of the length increment, the minor diameter of an increment substantially corresponding to the major diameter of a serially preceding increment.

12. A method as described by claim 11 wherein tissue extirpation along said canal length is substantially limited to the length of each conical frustrum, sequentially.

13. An endodontic instrument for extirpating radicular dental canals, said instrument including a shaft comprising:

a proximal end, a distal end, and a fluted working portion located between said proximal and distal ends, said fluted working portion including a tapered cutting surface located adjacent said distal end and increasing in diameter in a proximal direction from a minor diameter to a larger, major diameter, and a fluted proximal portion located between said tapered cutting surface and said proximal end, said fluted proximal portion having a zero taper angle configured to carry debris away from said distal end without substantially cutting tissue during a cutting movement of said shaft.

14. The endodontic instrument of claim 13, wherein said distal end forms a conical frustum.

15. The endodontic instrument of claim 13, wherein said distal end is a tip forming a substantial apex.

16. A set of endodontic instruments for extirpating radicular dental canals, each instrument in said set having a shaft with a proximal end, a distal end and a working length therebetween that includes a tapered cutting surface adjacent said distal end, said tapered cutting surface having a cutting length extending from a first diameter to a second, smaller diameter located at said distal end, the second diameter for a first instrument in said set substantially being an apex terminus and subsequent instruments in said set having a second diameter substantially corresponding to the first diameter of a sequentially adjacent instrument, at least one of said instruments including a fluted proximal portion located proximally of said tapered cutting surface and having a zero taper angle such that said fluted proximal portion carries debris away from said distal end without substantially cutting tissue during a cutting movement of said shaft.

17. A method of extirpating a radicular dental canal with an instrument including a shaft having a proximal end and a distal end defined along an axis of movement, and a fluted working portion located between the proximal and distal ends, the fluted working portion including a tapered cutting surface located adjacent the distal end and increasing in diameter in a proximal direction from a minor diameter to a larger, major diameter, and a fluted proximal portion located between the tapered cutting surface and the proximal end, the fluted proximal portion having a zero taper angle, the method comprising the steps of:

inserting the fluted working portion of the instrument into the radicular dental canal, cutting tissue within the radicular dental canal with the tapered cutting surface, and directing tissue debris away from the distal end along the fluted proximal portion.

* * * * *

UNITED STATES PATENT AND TRADEMARK OFFICE
CERTIFICATE OF CORRECTION

PATENT NO. : 6,293,794 B1
DATED : September 25, 2001
INVENTOR(S) : John T. McSpadden It is certified that error appears in the above-identified patent and that said Letters Patent is hereby corrected as shown below:

Column 2,
Line 37, reads "or cylindrical shaft to surfaces" and should read -- or cylindrical shaft surfaces --.

Column 5,
Lines 15 and 22, reads "d," and should read -- $d_1$ --.

Column 6,
Line 25, reads "100C and 100D" and should read -- 110C and 110D --.

Signed and Sealed this

Fourth Day of June, 2002

Attest:

JAMES E. ROGAN
Attesting Officer     Director of the United States Patent and Trademark Office